United States Patent [19]

Koivurinta

[11] Patent Number: 4,698,101

[45] Date of Patent: Oct. 6, 1987

[54] BINDER-DILUENT COMPOSITION AND METHOD

[75] Inventor: Juha A. Koivurinta, Helsinki, Finland

[73] Assignee: Suomen Sokeri Oy (Finnish Sugar Company Ltd.), Finland

[21] Appl. No.: 708,599

[22] Filed: Mar. 6, 1985

Related U.S. Application Data

[63] Continuation-in-part of Ser. No. 412,804, Aug. 30, 1982, abandoned.

[51] Int. Cl.$^4$ ............................ C13F 3/00; A23G 3/00
[52] U.S. Cl. .......................................... 127/30; 127/29; 426/658; 426/454; 426/453; 426/285; 514/23; 514/53
[58] Field of Search .................... 127/30, 29; 426/658, 426/454, 453, 285; 514/23, 53

[56] References Cited

U.S. PATENT DOCUMENTS 4,349,542  9/1982  Staniforth .
4,395,292  7/1983  Katz et al. ............................. 127/30

FOREIGN PATENT DOCUMENTS 35224  3/1979  Japan ..................................... 127/30

*Primary Examiner*—Andrew Metz
*Assistant Examiner*—Chung K. Pak
*Attorney, Agent, or Firm*—Brumbaugh, Graves, Donohue & Raymond

[57] ABSTRACT

A binder-diluent for direct compression tableting based on pulverized crystalline fructose is prepared by granulating the fructose with a small amount of a disaccharide syrup such as maltose syrup.

8 Claims, No Drawings

BINDER-DILUENT COMPOSITION AND METHOD

This application is a continuation-in-part of application Ser. No. 412,804, filed Aug. 30, 1982, now abandoned.

This invention relates to a binder-diluent for direct compression tableting, and particularly to a binder-diluent which consists of a granulated product which is prepared from a pulverized crystalline fructose and a small amount of a starch-based disaccharide syrup such as maltose syrup.

BACKGROUND OF INVENTION

A binder-diluent product for direct compression tableting must be free-flowing, compressible and palatable. Advantageous in tableting are water soluble sugar products. Sweet sugars as binder-diluents are preferable in chewable tablets, but crystalline or pulverized sugars are unsuitable for direct compression. Only special agglomerated or granulated sugar products can be used. Suitable binder-diluents for chewable tablets are, for example, spray-dried lactose, "Emdex", which is an agglomerated dextrose, "DiPac", which is an agglomerated sucrose with dextrins, mannitol, and direct compression starches.

Fructose has several advantages as binder-diluent in palatable tablets. The taste is sweet, the sugar is less cariogenic than sucrose, it is suitable for diabetics and the water solubility of fructose is good. Fructose is, however, not directly compressible. Agglomeration of fructose also presents problems. Fructose granules agglomerated from a water solution are hard and the compressibility is unsatisfactory. A granular fructose product has been prepared from a fructose-alcohol mixture; for example, see U.S. Pat. No. 3,684,573. The use of alcohols in tableting, however, calls for special precautions in industrial applications. It is therefore a great advantage if a compressible product can be prepared using only water as solvent. Such a product can be prepared by adding a comparatively large amount of dextrins to a fructose solution and spray-drying the mixture; see European patent application bearing publication No. 0036738, filed 3/16/81. This method does not provide a product that is predominantly fructose, but rather a sugar mixture including fructose as one of several carbohydrates.

STATEMENT OF INVENTION

We have now found that a free-flowing granular fructose product, suitable for use as a binder-diluent in direct compression tableting, is formed when pulverized fructose is agitated together with a small amount of a starch-based disaccharide syrup, such as maltose syrup.

Pulverized fructose is prepared from crystalline fructose by milling. It is preferred according to this invention that the fructose be pulverized to a mean particle size in the range of about 75-95 $\mu$m.

The disaccharide syrup used in agglomerating the fructose may be a starch-based disaccharide syrup such as maltose syrup. A starch-based maltose syrup is prepared by enzymatic hydrolysis of starch and contains less than 10% of glucose and at least 50% of maltose on dry substance.

The granulation is easily carried out in a conventional manner by adding to the pulverized fructose a starch-based disaccharide syrup, while the mixture is constantly agitated. In this manner the pulverized sugar is agglomerated to form granules within the preferred mean particle size range of about 0.15-0.60 mm. The granulated product is finally dried to a water content of less than 1%, preferably less than 0.5%.

It is important to the present invention that the material added during agglomeration be a starch-based disaccharide syrup. Water by itself provides unacceptable results. Furthermore, attempts to obtain suitable products using invert sugar of fructose solutions have not provided an acceptable product. It appears that the added sugar solution used for agglomeration should not contain fructose.

It is recognized in the art that the need for a lubricant in direct compression tableting processes depends on the type of machine employed, as well as the composition of the final tablet, and similar considerations apply in employing the compositions and methods of the present invention. Where needed, a prior art lubricant, such as magnesium stearate at a 0.5% level, by weight, may be employed.

The composition of the product of this invention, by weight, is as follows:

| | |
|---|---|
| Fructose | about 80-98%, preferably about 90-95% |
| Disaccharide | about 2-20%, preferably about 3-6% |
| Other Saccharides | about 0-10%, preferably no more than about 8% |

The product is free-flowing and compressible and meets the requirements for a high quality tableting binder-diluent material.

The following Examples further illustrate the process and product of the present invention:

EXAMPLE 1

Raw materials:

Pulverized U.S. pharmacopea grade fructose with a mean particle size of 95 $\mu$m.

Diluted maltose syrup prepared by enzymatic hydrolysis of starch, with maltose 58% and glucose 2.5% of the dry substance (HPLC-analysis).

40 kg of the pulverized fructose was agitated in a rotating granulator. 3 liters of diluted maltose syrup, 75 weight %, was added from a spray nozzle to the fructose with agitation. The agitation was continued for 30 minutes with a speed of 24 r/minute. A granular product was formed, which had a mean particle size of 0.45 mm (C.V. 44%). The granules were dried in a fluidized bed dryer to a water content of less than 0.50%.

Tablets were prepared from the granulate by direct compression and the tablets tested according to European Pharmacopoea methods.

| Results were as follows: | |
|---|---|
| Diameter of Tablets | 10 mm |
| Mean weight | 525 mg |
| Percentage deviation | <5% of 100 tablets |
| Disintegration | 4.5 minutes |

EXAMPLE 2

A fructose binder-diluent was made using the raw materials and equipment described in Example 1.

40 kg of the pulverized fructose was sprayed with 2.5 liters of 70 weight % maltose syrup, while the mixture was constantly agitated. The agitation was continued for 40 minutes. The formed granules were dried to a water content of less than 0.50%. The mean particle size of the product was 0.50 mm (C.V. 49%).

Tablets were prepared from the granules by direct compression. Evaluation of the tablets gave the following

| results: | |
| --- | --- |
| Diameter of tablets | 10 mm |
| Mean weight | 525 mg |
| Percentage deviation | <5% of 100 tablets |
| Disintegration | 4 minutes |

The test results showed that the granules were directly compressible to form tablets with satisfactory properties.

I claim:

1. A fructose-based dry binder-diluent for use in making direct compression tablets comprising a plurality of compressible free-flowing granules having a mean particle size in the range of about 0.15–0.60 mm, the granules having been formed by agglomeration of pulverized crystalline fructose with a maltose-containing syrup, followed by drying, and the granules containing by weight about 80–98% of fructose, about 2–20% disaccharide and up to 1.0% water.

2. The product of claim 1 wherein fructose is present at a level of about 89–97%, maltose is present at a level in the range of about 3–6% the percentages being by weight of the binder-diluent.

3. The product of claim 1 wherein said maltose containing syrup contains other saccharides which are present at a level up to about 8%, said percentage being by weight of the binder-diluent.

4. The product of claim 1, further comprising a lubricant suitable for use in a direct compression tableting process.

5. The product of claim 4, wherein the lubricant is magnesium stearate.

6. A fructose-based dry binder-diluent for use in making direct compression tablets comprising a plurality of compressible free-flowing granules of mean particle size in the range of about 0.15–0.60 mm, the granules having been formed by agitation of pulverized, crystalline fructose while adding thereto a maltose-containing syrup in finely divided form, followed by drying, the granules containing, by weight, about 80–98% of fructose, about 2–20% maltose and up to 1.0% water.

7. The product of claim 6 wherein fructose is present at a level of about 89–97%, the maltose is present at a level in the range of about 3–6% the percentages being by weight of the binder-diluent.

8. The product of claim 6 wherein said maltose containing syrup contains other saccharides which are present at a level up to about 8%, said percentage being by weight of the binder-diluent.

* * * * *

UNITED STATES PATENT AND TRADEMARK OFFICE
CERTIFICATE OF CORRECTION

PATENT NO.  : 4,698,101
DATED       : October 6, 1987
INVENTOR(S) : Juha A. Koivurinta It is certified that error appears in the above-identified patent and that said Letters Patent is hereby corrected as shown below:

On the front page, below "U.S. Patent Documents", insert:

--3,684,573   8/1972   Voigt              127/30

3,365,331   1/1968   Miller et al.      127/30

4,220,666   9/1980   Fields             476/285X 3,836,396   9/1974   McNamara et al.    127/30

4,007,052   2/1977   Heinemann et al.   127/30

4,199,373   4/1980   Dwivedi et al.     127/30

3,718,484   2/1973   Glabe              127/30

4,352,821   10/1982  Doran et al.       514/713

4,271,199   6/1981   Cherukuri et al.   426/658X--

UNITED STATES PATENT AND TRADEMARK OFFICE
CERTIFICATE OF CORRECTION

PATENT NO. : 4,698,101
DATED : October 6, 1987
INVENTOR(S) : Juha A. Koivurinta

It is certified that error appears in the above-identified patent and that said Letters Patent is hereby corrected as shown below:

On the front page below the last foreign patent listed, insert:

```
--1,463,288   2/1977 Great Britain
     990,130  6/1976 Canada
   0,036,738  3/1981 European
   1,240,433  7/1971 Great Britain    127/30
   5,321,113  2/1978 Japan            127/30
```

Other Publications

Lachman, Food Engineering, May 1966, pps. 140, 143, 145.--

Column 3, line 7, after "ing" insert -- results: --.
Column 3, line 10, delete "results:".

Signed and Sealed this

Twelfth Day of April, 1988

Attest:

DONALD J. QUIGG

Attesting Officer

Commissioner of Patents and Trademarks